United States Patent [19]

Ribi et al.

[11] Patent Number: 4,520,019

[45] Date of Patent: May 28, 1985

[54] STABLE COMPOSITION AND PREPARATION THEREOF

[75] Inventors: Edgar E. Ribi; John L. Cantrell, both of Hamilton; Steven M. Schwartzman, Stevensville, all of Mont.

[73] Assignee: Ribi ImmunoChem Research, Inc., Hamilton, Mont.

[21] Appl. No.: 591,230

[22] Filed: Mar. 19, 1984

Related U.S. Application Data

[63] Continuation of Ser. No. 372,844, Apr. 29, 1982, abandoned.

[51] Int. Cl.[3] ...................... A61K 35/78; A61K 39/02
[52] U.S. Cl. ..................................... 424/195.1; 624/92
[58] Field of Search .................................. 424/195, 92

[56] References Cited

U.S. PATENT DOCUMENTS 4,010,257 3/1977 Adlam et al. ......................... 424/92
4,152,423 5/1979 Adam et al. ......................... 424/92

OTHER PUBLICATIONS

Megen et al., J. Nat. Canc. Inst., 52: 103-108, 1974.
Azuma et al., J. Nat. Canc. Inst., 52: 95-100, 1974.

*Primary Examiner*—Jerome D. Goldberg
*Assistant Examiner*—John W. Rollins, Jr.
*Attorney, Agent, or Firm*—Burgess, Ryan & Wayne

[57] ABSTRACT

A stable composition containing cell wall skeleton (CWS) and trehalose dimycolates (TDM) which may be effectively reconstituted after lyophilization. The composition is useful in the treatment of various cancerous tumors in animals without side effects. Also disclosed is a method of producing the composition and a method of treating cancerous tumors in animals using said composition.

7 Claims, No Drawings

STABLE COMPOSITION AND PREPARATION THEREOF

This application is a continuation of application Ser. No. 372,844, filed Apr. 29, 1982, now abandoned.

BACKGROUND OF THE INVENTION

The subject matter of the present invention is directed to a stable, therapeutically effective composition containing cell wall skeleton (CWS) and purified trehalose dimycolates (TDM). Both substances are isolates of bacteria and when used together as a composition, are effective in obtaining suppression and regression of tumor cells. The present invention also includes a method of preparing the composition as well as use of the composition in treating cancerous tumors and as an adjuvant.

The combination of CWS and TDM is known in the art (See *Biologically Active Components from Mycobacterial Cell Walls. II. Suppression and Regression of Strain-2 Guinea Pig Hepatoma*; Meyer et al., Journal of the National Cancer Institute, Volume 52, No. 1, January, 1974; and *Mycobacterial Cell Wall Components in Tumor Suppression and Regression;* Ribi et al., National Cancer Institute Monograph No. 39, pgs. 115–120, October, 1972) incorporated herein by reference.

Cell Wall Skeleton is essentially cell wall which has had much of the protein and lipids normally found in the cell wall removed. It is a polymeric mycolic acid—arabinogalactan mucopeptide containing remnants of trehalose mycolates ("P$_3$") and undigested tuberculoproteins. Cell wall skeleton is obtained from any mycobacteria including, but not limited to, M.smegmatis, M.phlei, M.avium, *Nocardia rubra, Nocardia asteroides, Corynebacterium diphtheriae, Corynebacterium parvum,* M.bovinis, M.kansasii, M. tuberculosis (Strain H 37 RV and Ayoma B), and M.Bovis Strain BCG. Additionally, cell wall skeleton may be obtained from such non-mycobacteria as E.coli, B.abortus and *Coxiella burnettii.*

The process of producing cell wall skeleton is time consuming. The bacteria such as M.Bovis Strain BCG (Bacillus Calmette-Guerin) is grown and harvested. The resulting whole cell residue is processed through a cell fractionator [Ribi Cell Fractionator (Sorvall, Model RF-1)] which disrupts the cells, separating the outer envelope or cell wall from the protoplasmic impurities. The resulting cell walls are then subjected to a series of solvent extractions and enzymatic treatments (e.g., trypsin and/or chymotrypsin) to give purified cell wall skeleton.

The second component of the instant composition, trehalose dimycolates (TDM), may be obtained from any mycobacteria as, for example, M.avium, M.phlei, M.tuberculosis (Strain H 37 RV and Ayoma B), M.bovis BCG, M.smegmatis, M.kansasii, *Nocardia rubra,* M.bovinis and *Corynebacterium diphtheriae.*

Bacteria such as M.avium is grown, harvested and then heat killed. The cell mass is then extracted with several solvents and then an active, solvent soluble, fraction is extracted. This extract is further purified by a series of solvent extractions to provide crude TDM (See *Biologically Active Components from Mycobacterial Cell Walls. I. Isolation and Composition of Cell Wall Skeleton and Component P$_3$*; Azuma, et al., Journal of the National Cancer Institute, Volume 52, pgs. 95–101, 1974) incorporated herein by reference. As disclosed in Azuma et al, crude TDM may then be further purified by centrifugal microparticulate silica gel chromatography to give purified TDM.

CWS and TDM produced as described above have been combined in an oil droplet emulsion. The non-living components are ground with a small amount of mineral oil and emulsified in saline to produce an anti-animal tumors composition suitable for injection (See *Immunotherapy with Non-viable Microbial Components,* Ribi, et al.; Annals of the National Academy of Sciences, Volume 227, pgs. 228–238, Sept. 20th, 1976) incorporated herein by reference.

However, the prior art oil in saline emulsions containing CWS and TDM suffer from a major disadvantage. The emulsion has a relatively short shelf life at room temperature and, therefore, must be used shortly after preparation to produce the desired results.

It is well-known in the art that lyophilizing a pharmaceutical preparation can extend shelf life considerably (See, for example, U.S. Pat. No. 3,932,943; U.S. Pat. No. 3,594,471; and U.S. Pat. No. 4,134,214). To be successful, the lyophilized product must be able to be reconstituted at a later time without any loss in potency, that is, with the same potency as the pre-lyophilized product. However, the prior art CWS-TDM oil in saline emulsions have not been effectively lyophilized. Applicants have discovered that if these emulsions are not stabilized without delay, as, for example, by lyophilization, they will begin a process of degradation resulting in a significant percent of oil droplets becoming uncoated. The uncoated material is not active in tumor regression. The therapeutically effective emulsion of the present invention is stabilized by a lyophilization procedure; other stabilization procedures can also be utilized.

It is therefore an object of the invention to provide a stable CWS-TDM composition which may be effectively reconstituted to produce an effective anti-animal tumors preparation having a superior shelf life that is, a shelf life of a year and even longer. It is another object of the invention to provide a CWS-TDM composition having a large numer of coated oil droplets which are very effective in tumor regression, without side effects.

It is still another object of the invention to provide a method of treating various cancer tumors with a stable and potent CWS-TDM composition. It is another object of the invention to employ the CWS-TDM composition as an adjuvant as for example, to increase the immune response to immunogens including, for example, microorganisms, proteins, carbohydrates, allergens, viruses and the like.

THE INVENTION

The present invention is directed to a stable composition comprising CWS and TDM in which the active materials are coated on oil droplets. The composition may be effectively reconstituted in an aqueous solution with the same potency as in the pre-lyophilized state.

The process of producing the instant composition comprises mixing CWS and TDM for a time sufficient to form a uniform suspension. If desirable, the TDM may be dissolved in a suitable solvent known to those skilled in the art. For example, such solvents include chloroform, ether, methanol, ethanol, combinations thereof and the like. The weight ratio of CWS to TDM is in the range of between about 1.0:1 and 6:1, preferably between about 2.5:1 and 3.0:1.

A light, non-biodegradable oil is then added and the resulting mixture is homogenized to form a paste-like substance.

The use of a light hydrocarbon non-biodegradable oil is an essential element of the process since biodegradable oils do not achieve the objects of the invention. Furthermore, the oil must be light weight typically having a viscosity of between about 8 and 12 centistokes measured at 100° F. Preferably, the viscosity is in the range of between about 10 and 10.6 centistokes.

The amount of oil used in the process is in the range of between about 0.5 and 3.0 percent by volume based on the total volume of the composition. It is preferred to use between about 0.75 and 1.5 percent by volume of the oil. Examples of such oils include light mineral oil, squalane, 7-n-hexyloctadecane, Conoco superoil and Drakeol 6 VR mineral oil (produced by the Pennreco Company, Butler, Pa.).

The homogenized oil containing mixture is then combined with a detergent which may optionally be dissolved in a saline solution prior to mixing. The amount of detergent is typically between about 0.02 and 0.20 percent by volume and preferably between about 0.10 and 0.20 percent by volume based on the total volume of the composition. Any common detergent material may be used including Tween-80, and Arlacel (produced by the Atlas Chemical Company).

The mixture resulting from the addition of detergent is then homogenized to form a suspension which has a high percentage of oil droplets coated with CWS and TDM as determined by observation under a microscope.

The novel composition of the present invention is an effective agent in the treatment of cancerous tumors in animals and the composition, in the form of an oil droplet emulsion, is injected directly into the tumor tissue. Cancers which can be treated include bovine fibrosarcoma, equine sarcoid, equine melanoma, canine malanoma, and bovine ocular sarcoma. The daily dosage of the composition to a typical adult patient weighing about 70 kilograms is sufficient to provide about 150–300 ug of CWS and 50–100 ug of TDM. Therapy may be continued for approximately two to six months providing a total dosage of up to 15 mg of CWS and 15 mg. of TDM.

The instant composition, when used to increase a response to immunogens, is administered at a dosage of between about 10 and 500 micrograms. CWS and TDM can also be used separately as adjuvants; each in amounts of about 10 to about 500 micrograms.

DESCRIPTION OF THE PREFERRED EMBODIMENTS

The following examples are for illustrative purposes only and are not intended to limit or in any way redefine the invention as claimed in the claims appended hereto.

EXAMPLE 1

Preparation of CWS-TDM Composition 150 mg of CWS were introduced into a 350 ml tissue homogenizer (Bellco). 50 mg of TDM were dissolved in 2.5 ml of a 95:5 chloroform-methanol mixture and then added to the homogenizer. The resulting CWS-TDM suspension was mixed for about 15 to 30 seconds and the solvent was evaporated using a sterile air stream. This was followed by the addition of 2 ml of sterile Drakeol 6 VR mineral oil (Pennreco Company, Butler, Pa.) and the mixture was homogenized for 1 minute using a drill press while an oil paste consistency is obtained. 190 ml of 0.2 percent Tween-80 in saline solution was introduced into the each homogenizer. Using a drill press, the mixture was homogenized for about 4 to 5 minutes until an emulsion was obtained. Microscopic investigation showed that substantially all of the oil droplets were coated with CWS and TDM.

EXAMPLE 2

Lyophilizing the CWS-TDM Composition 5 ml of the CWS-TDM oil in saline emulsion (a 1% oil-in-water emulsion) produced in accordance with the procedure of Example 1 was introduced into a 10 ml Wheaton serum vial. The vial was frozen in a Revco freezer at a temperature of −95° C. and lyophilized in a sterile container on a Labconco freeze dryer. The vial was then capped using a sterile technique.

EXAMPLE 3

Reconstitution of Lyophilized CWS-TDM Composition

A vial containing the lyophilized CWS-TDM emulsion produced in accordance with the procedure of Example 2 containing, for example, 3.75 mg CWS and 1.25 mg TDM in 5 ml. of a 1% oil droplet emulsion was injected with sterile distilled water using a No. 20 gauge sterile syringe. The suspension was then emulsified by repeated aspirations and injections using the syringe for at least two minutes until the resulting emulsion gave a cloudy-milky appearance.

EXAMPLE 4

CWS-TDM Composition-Comparison Data (Animals)

| | Dose per Animal (μg) (guinea pig)* | Animals Treated | % Regression |
|---|---|---|---|
| CWS + TDM | 300 + 150 | 125 | 76 |
| CWS | 300 | 157 | 46 |
| CWS + TDM | 150 + 150 | 56 | 63 |
| CWS | 150 | 65 | 43 |
| CWS + TDM | 50 + 50 | 16 | 19 |
| CWS | 50 | 40 | 10 |
| TDM | 150 | 39 | 3 |
| TDM | 100 | 22 | 0 |
| Oil-tween-saline controls | — | 66 | 0 |

*Strain 2
The CWS was obtained from M. bovis.

What we claim is:

1. A method for producing a stable composition containing cell wall skeleton (CWS) and trehalose dimycolate (TDM) comprising:

(a) mixing CWS and TDM useful for treating tumors selected from the group consisting of bovine fibrosarcoma, equine sarcoid, equine melanoma, canine melanoma and bovine ocular sarcoma in a weight ratio of CWS to TDM of between about 1.0:1 and 6:1;

(b) adding a light hydrocarbon non-biodegradable oil to the resulting mixture; wherein said light hydrocarbon non-biodegradable oil has a viscosity of between about 8 and 12 centistokes measured at 100° F. and is present in an amount between about 0.5 and 3.0 percent by volume based on the total volume of the composition;

(c) homogenizing the resulting oil containing mixture;

(d) adding a detergent in an amount of between about 0.02 and 0.20 percent by volume based on the total volume of the composition selected from the group consisting of polyoxyethylene sorbition mono oleates and non-ionic emulsifiers of fatty acid polyols and polyanhydrides to said homogenized oil containing mixture;

(e) homogenizing the resulting mixture to form an emulsion containing oil droplets coated with CWS and TDM;

(f) lyophilizing the resulting emulsion and subsequently reconstituting said emulsion with sterile distilled water.

2. The method of claim 1, wherein said ratio is between about 2.5:1 and 3.5:1.

3. The method of claim 1 wherein said light hydrocarbon non-biodegradable oil is present in an amount between about 0.75 and 1.5 percent by volume.

4. The method of claim 1, wherein the amount of said detergent is between about 0.10 and 0.20 percent by volume based on the total volume of the composition.

5. A pharmaceutical composition prepared by the method of claim 1.

6. The composition of claim 5 wherein said weight ratio is between about 2.5:1 and 3.5:1.

7. A method of treating cancerous tumors selected from the group consisting of bovine fibrosarcoma, equine sarcoid, equine melanoma, canine melanoma and bovine ocular sarcoma comprising administering by injection a therapeutically effective amount of the composition of claim 5 to a warm-blooded animal.

* * * * *